United States Patent [19]

McAvinn et al.

[11] 4,428,488
[45] Jan. 31, 1984

[54] DEVICE FOR SUPPORTING SPONGE COLLECTION BAGS

[75] Inventors: James D. McAvinn, Palatine; Felipe S. Li, Lake Zurich, both of Ill.

[73] Assignee: The Kendall Company, Boston, Mass.

[21] Appl. No.: 295,337

[22] Filed: Aug. 24, 1981

[51] Int. Cl.³ .............................................. A47F 5/01
[52] U.S. Cl. ..................................... 211/181; 211/86; 211/112; 248/230; 248/311.3
[58] Field of Search .................... 211/50, 86, 87, 88, 211/71, 107, 181, 106, 119, 112; 248/218.4, 226.4, 311.3, 95, 230; D6/86, 184, 194

[56] References Cited

U.S. PATENT DOCUMENTS

| | | | |
|---|---|---|---|
| 713,751 | 11/1902 | Conn | 211/119 |
| 2,505,212 | 4/1950 | Schneider | 211/119 X |
| 2,739,834 | 3/1956 | Bryce | 248/230 X |
| 2,972,416 | 2/1961 | De Vivo | 211/181 X |
| 2,972,417 | 2/1961 | Smith | 211/181 X |
| 3,414,223 | 12/1968 | Pawsat | 248/230 |
| 3,425,127 | 2/1969 | Long et al. | 248/230 X |
| 4,030,690 | 6/1977 | Honauer et al. | 248/311.3 |
| 4,146,138 | 3/1979 | Davis | 248/226.4 |
| 4,339,060 | 7/1982 | Braida | 248/313 X |

FOREIGN PATENT DOCUMENTS 1371949  8/1964  France .................... 211/86

OTHER PUBLICATIONS

Two photographs, cited by applicant, of a device admitted to be a reference under 35USC102(a).

Primary Examiner—Ramon S. Britts
Assistant Examiner—Robert W. Gibson, Jr.
Attorney, Agent, or Firm—Powell L. Sprunger

[57] ABSTRACT

A device for supporting sponge collection bags from a pole comprising, a basket having opposed front and back sides, a pair of opposed ends connecting the sides, a bottom, and an open top. The sides, ends and bottom define a cavity to receive a box of sponge collection bags through the open top. The basket has a pair of spaced hooks depending from the front side and being directed away from the front side, and a pair of spaced hooks depending from the back side and being directed away from the back side, with the hooks being adapted to be received in spaced apertures of the sponge collection bags. The device has a support member for supporting the basket on the pole.

2 Claims, 5 Drawing Figures

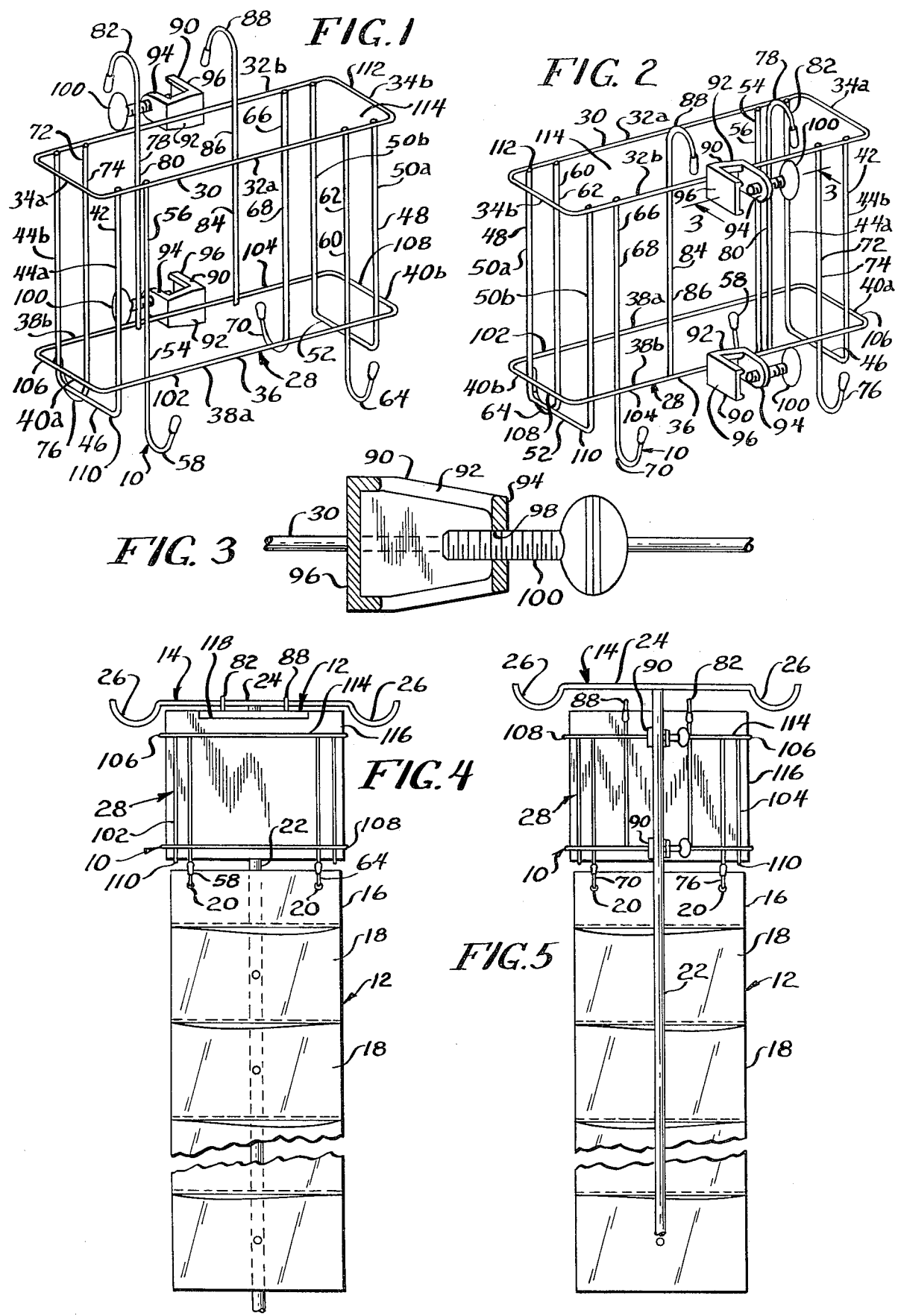

DEVICE FOR SUPPORTING SPONGE COLLECTION BAGS

BACKGROUND OF THE INVENTION

The present invention relates to devices for supporting sponge collection bags.

During surgical procedures, absorbent sponges are utilized to absorb body fluids around the site of the surgical incision. The sponges are normally provided in two sizes, a 4-inch by 4-inch smaller sponge, and a 14-inch by 14-inch larger laparotomy sponge. In the past, when the wetted sponges were removed from the patient's body, they have been placed in a kick bucket for retention during the surgical procedure. At the end of the surgical procedure, the sponges were removed from the kick bucket, and were sorted according to size, after which they were counted to assure that no sponges were left in the patient's body. According to convention, the 4-inch by 4-inch sponges were counted in groups of ten, and the 14-inch by 14-inch sponges were counted in groups of five.

It will be apparent that the prior sorting and counting procedure was tedious and time consuming, and could be subject to error during the counting of sponges. A sponge collection bag with pockets has been proposed in U.S. Pat. No. 3,749,237 in an attempt to facilitate this procedure, and it is desirable to support the bags during a surgical procedure.

SUMMARY OF THE INVENTION

A principal feature of the present invention is the provision of a device for supporting sponge collection bags.

The device has a basket having opposed front and back sides, a pair of opposed ends connecting the sides, a bottom, and an open top, with the sides, ends and bottom defining a cavity to receive a box of sponge collection bags through the open top. The basket has a pair of spaced hooks depending from the front side and being directed away from the front side, and a pair of spaced hooks depending from the back side and being directed away from the back side.

A feature of the present invention is that the hooks may be received in spaced apertures of the sponge collection bags in order to support the bags from the basket.

Another feature of the invention is the provision of clamp means on the back side for securing the basket on an I.V. pole.

Further features will become more fully apparent in the following description of the embodiments of this invention and from the appended claims.

DESCRIPTION OF THE DRAWINGS

In the drawings:

FIG. 1 is a front perspective view of a bag supporting device of the present invention;

FIG. 2 is a rear perspective view of the supporting device of the present invention;

FIG. 3 is a fragmentary sectional view taken substantially as indicated along the line 3—3 of FIG. 2;

FIG. 4 is a front elevational view showing the device being supported on the crossbar of an I.V. pole; and FIG. 5 is a rear elevational view showing the device being supported on the upright bar of an I.V. pole.

DESCRIPTION OF THE PREFERRED EMBODIMENTS

Referring now to FIGS. 1-5, there is shown a device generally designated 10 for supporting sponge collection bags 12 from an I.V. pole 14. The bags 12 are made from a suitable thermoplastic material, and the bags 12 have a backing sheet 16, and a plurality of pockets 18 disposed along the backing sheet 16. The bags 12 also have a pair of spaced apertures 20 in an upper portion of the backing sheet 16 as will be discussed below. The I.V. pole has an upright bar 22, and a crossbar 24 supported by the upper end of the upright bar 22, with the crossbar 24 having pigtails 26 at opposed outer ends of the crossbar 24.

The device 10 has a basket 28 constructed from wire members, as shown in FIGS. 1-3. The basket 28 has a first horizontal wire 30 having opposed side portions 32a and 32b, and a pair of opposed end portions 34a and 34b connecting the side portions 32a and b. The basket 28 also has a second horizontal wire 36 spaced from the first horizontal wire 30. The second horizontal wire 36 has a pair of opposed side portions 38a and 38b, and a pair of opposed end portions 40a and 40b connecting the side portions 38a and b. As shown, the first horizontal wire 30 is located at an upper end of the basket 28, while the second horizontal wire 36 is located adjacent a lower portion of the basket 28.

The basket 28 has a first vertical wire 42 having a pair of opposed upright side portions 44a and 44b, and a bottom portion 46 connecting the side portions 44a and b. The basket 28 has a second vertical wire 48 having opposed upright side portions 50a and 50b, and a bottom portion 52 connecting the side portions 50a and b. As shown, upper ends of the side portions 44a and b and 50a and b of the wires 42 and 48, respectively, are secured to the side portions 32a and b of the wire 30 adjacent the end portions 34a and b. Also, lower parts of the side portions 44a and b and 50a and b of the wires 42 and 48, respectively, are secured to the side portions 38a and b of the wire 36 adjacent the end portions 40a and b. The wires may be secured together by any suitable means, such as by welding.

The basket 28 has a third vertical wire 54 having a side portion 56, and a hook 58 at a lower end of the wire 54. The basket 28 has a fourth vertical wire 60 with a side portion 62 and a hook 64 at a lower end of the wire 60. The basket 28 has a fifth vertical wire 66 having a side portion 68 and a hook 70 at a lower end of the wire 66. The basket 28 also has a sixth vertical wire 72 having a side portion 74 and a hook 76 at a lower end of the wire 72. As shown, upper ends of the side portions 56, 62, 68, and 74 of the wires 54, 60, 66, and 72, respectively, are secured to the side portions 32a and b of the first wire 30. Also, lower parts of the side portions 56, 62, 68, and 74 of the wires 54, 60, 66, and 72, respectively, are secured to the side portions 38a and b of the wire 36, with the wires 54, 60, 66, and 72 being located adjacent the opposed end portions 34a and b and 40a and b of the wires 30 and 36, respectively.

The basket 28 has a seventh vertical wire 78 having a side portion 80, and a hook 82 at an upper end of the wire 78. The basket 28 also has an eighth vertical wire 84 having a side portion 86, and a hook 88 at an upper end of the wire 84. As shown, lower ends of the side portions 80 and 86 of the wires 78 and 84, respectively, are secured to the side portion 38b of the wire 36. Upper parts of the side portions 80 and 86 of the wires 78 and 84, respectively, are secured to the side portion 32b of the wire 30, with the wires 78 and 84 being located on opposed sides of a lateral central portion of the basket 28, and with the wires 78 and 84 being located adjacent the central portion of the basket 28.

The basket 28 has a pair of vertically spaced clamps 90. The clamps 90 have a back portion 92, and a pair of spaced flanges 94 and 96 extending from opposed ends of the back portion 92. The flanges 94 have a threaded opening 98, and a threaded bolt 100 received in the openings 98, such that the bolts 100 may be adjusted in the openings 98. As shown, the back portions 92 of the clamps 90 are secured to the side portions 32b and 38b of the wires 30 and 36, respectively, at a central portion of the wires 30 and 36.

The described wires define a front side 102, an opposed back side 104, a pair of opposed ends 106 and 108 connecting the sides 102 and 104, a bottom 110, and an open top 112. As shown, the sides 102 and 104, the ends 106 and 108, and the bottom 110 define a cavity 114. In the described configuration, the hooks 58 and 64 depend from the front side 102, with the hooks 58 and 64 being directed outwardly from the front side 102. Also, the hooks 70 and 76 depend from the back side 104, and are directed outwardly from the back side 104. The hooks 82 and 88 extend upwardly from the back side 104, and are directed outwardly from the back side 104.

With reference to FIG. 4, the hooks 82 and 88 may be utilized to support the basket 28 on the crossbar 24 of the I.V. pole 14. Alternatively, with reference to FIG. 5, the clamps 90 may be secured to the upright bar 22 of the pole 14 in order to secure the basket 28 to the pole 14. Thus, the clamps 90 permit adjustment of the basket 28 to the height of the nurse, or placement of the basket at or below table level, if desired. With reference to FIGS. 4 and 5, a box 116 containing folded sponge collection bags 12 may be inserted into the cavity 114 of the basket 28 in order to support the box 116 on the pole 14. The bags 12 may be removed one at a time through an opening 118 at an upper end of the box 116. Next, the bags 12 may be placed on the hooks 58 and 64 and the hooks 70 and 76 with the openings 20 of the bags 12 received on the hooks in order to support the bags 12 from the opposed sides of the basket 28. Thus, the bags 12 are supported in a vertical position on opposed sides of the basket 28 in position where soiled sponges may be readily placed in the pockets 18 of the bags 12 during a surgical procedure. After the surgical procedure has been completed, the sponges may be readily counted through use of the number of pockets 18 on the bags 12 which are filled with sponges. The bags 12 may be removed from the hooks of the basket 28, and the bags containing the soiled sponges may be discarded in order to prepare the basket 28 for a further surgical procedure.

The foregoing detailed description is given for clearness of understanding only, and no unnecessary limitations should be understood therefrom, as modifications will be obvious to those skilled in the art.

We claim:

1. A device for supporting sponge collection bags from a pole, comprising:

a basket having opposed front and back sides, a pair of opposed ends connecting said sides, a bottom, an open top, with said sides, ends and bottom defining a cavity to receive a box of sponge collection bags through the open top, said basket having a pair of spaced hooks depending from said front side and being directed away from the front side, and a pair of spaced hooks depending from said back side and being directed away from the back side, with said hooks being adapted to be received in spaced apertures of the sponge collection bags, said hooks having an inner portion connected to the basket and an outer end portion being spaced from said inner portion;

means for supporting the basket on the pole and a sponge collection bag received on said front hooks.

2. The device of claim 1 wherein the supporting means comprises a pair of spaced hooks extending upwardly from said back side and being directed away from the back side, with said upward hooks being spaced closely from a center of the basket on opposed sides of the center.

* * * * *